United States Patent
Righini et al.

(10) Patent No.: US 10,937,560 B2
(45) Date of Patent: Mar. 2, 2021

(54) BEAM-LIMITING DEVICE FOR RADIOGRAPHIC APPARATUSES

(71) Applicant: CEFLA SOCIETÁ COOPERATIVA, Imola (IT)

(72) Inventors: Dario Righini, Imola (IT); Sergio Salsini, Imola (IT); Francesco Sciarra, Imola (IT)

( * ) Notice: Subject to any disclaimer, the term of this patent is extended or adjusted under 35 U.S.C. 154(b) by 165 days.

(21) Appl. No.: 15/472,583

(22) Filed: Mar. 29, 2017

(65) Prior Publication Data
US 2017/0287581 A1 Oct. 5, 2017

(30) Foreign Application Priority Data

Mar. 30, 2016 (IT) .................. 102016000032291

(51) Int. Cl.
| | | |
|---|---|---|
| *A61B 6/03* | (2006.01) | |
| *A61B 6/06* | (2006.01) | |
| *A61B 6/14* | (2006.01) | |
| *G21K 1/02* | (2006.01) | |
| *G21K 1/04* | (2006.01) | |
| *A61B 6/00* | (2006.01) | |

(52) U.S. Cl.
CPC .............. *G21K 1/025* (2013.01); *A61B 6/032* (2013.01); *A61B 6/035* (2013.01); *A61B 6/06* (2013.01); *A61B 6/14* (2013.01); *A61B 6/501* (2013.01); *G21K 1/02* (2013.01); *G21K 1/04* (2013.01); *G21K 1/043* (2013.01); *G21K 1/046* (2013.01)

(58) Field of Classification Search
CPC ............ G21K 1/02; G21K 1/025; G21K 1/04; G21K 1/043; G21K 1/046; A61B 6/06; A61B 6/032; A61B 6/035; A61B 6/14; A61B 6/501

USPC ...................................... 378/146–152, 38–40
See application file for complete search history.

(56) References Cited

U.S. PATENT DOCUMENTS

| | | | | |
|---|---|---|---|---|
| 4,672,652 A | 6/1987 | Huettenrauch | | |
| 6,215,853 B1 * | 4/2001 | Kump | ...................... | A61B 6/06 378/147 |
| 6,301,334 B1 * | 10/2001 | Tybinkowski | ........... | A61B 6/06 378/147 |
| 6,396,902 B2 * | 5/2002 | Tybinkowski | ......... | G21K 1/025 378/148 |
| 6,459,770 B1 * | 10/2002 | Tybinkowski | ........... | A61B 6/06 378/147 |
| 6,556,657 B1 * | 4/2003 | Tybinkowski | ........... | G21K 1/02 378/147 |
| 6,647,092 B2 * | 11/2003 | Eberhard | .................. | G21K 1/04 378/150 |
| 6,711,236 B2 * | 3/2004 | Izuhara | .................. | A61B 6/035 250/505.1 |

(Continued)

FOREIGN PATENT DOCUMENTS

JP 2001029339 2/2001

*Primary Examiner* — Allen C. Ho

(74) *Attorney, Agent, or Firm* — Themis Law

(57) ABSTRACT

A method of limiting a X-ray beam, for example in connection with an extraoral radiographic apparatus, includes moving at least two blades of a blade limiting device through one actuator only, so as to produce a X-ray beam having the desired shape, wherein the actuator moves the at least two blades at the same time, in a direct way and in the same direction, even in the event of inversion of the direction of movement of the blades.

15 Claims, 14 Drawing Sheets

(56) References Cited

U.S. PATENT DOCUMENTS

| | | | |
|---|---|---|---|
| 6,778,636 B1* | 8/2004 | Andrews | G21K 1/04 378/147 |
| 7,170,975 B2* | 1/2007 | Distler | A61B 6/032 378/147 |
| 7,206,383 B2* | 4/2007 | Zhao | G21K 1/04 378/148 |
| 7,212,611 B2* | 5/2007 | De Godzinsky | A61B 6/06 378/150 |
| 7,397,903 B2* | 7/2008 | Yang | G21K 1/04 378/147 |
| 7,508,918 B2* | 3/2009 | Liu | G21K 1/04 378/147 |
| 7,706,508 B2* | 4/2010 | Arenson | G21K 1/04 378/158 |
| 7,711,085 B2* | 5/2010 | Suzuki | A61B 6/14 378/39 |
| 7,852,990 B2* | 12/2010 | Aulbach | G21K 1/04 378/148 |
| 7,945,016 B2* | 5/2011 | Bothorel | A61B 6/14 378/38 |
| 7,970,099 B2* | 6/2011 | Fadler | G21K 1/046 378/124 |
| 8,005,187 B2* | 8/2011 | Suzuki | A61B 6/501 378/39 |
| 8,009,794 B2* | 8/2011 | Partain | A61B 6/035 378/7 |
| 8,064,568 B2* | 11/2011 | Von Der Haar | A61B 6/032 378/147 |
| 8,085,903 B2* | 12/2011 | Thomas | G21K 1/04 378/152 |
| 8,130,901 B2* | 3/2012 | Müller | A61B 6/06 378/147 |
| 8,199,884 B2* | 6/2012 | Junjie | G21K 1/04 378/160 |
| 8,503,604 B2* | 8/2013 | Inglese | A61B 6/14 378/40 |
| 8,824,638 B2* | 9/2014 | Nicholson | A61B 6/06 378/150 |
| 9,014,341 B2* | 4/2015 | Zhang | A61B 6/03 378/147 |
| 9,020,103 B2* | 4/2015 | Grodzins | G21K 1/046 359/223.1 |
| 9,044,176 B2* | 6/2015 | Loustauneau | A61B 6/488 |
| 9,111,656 B2* | 8/2015 | Schmidt | G21K 1/04 |
| 9,125,572 B2* | 9/2015 | Noo | A61B 6/027 |
| 9,198,626 B2* | 12/2015 | Heuscher | A61B 6/482 |
| 9,237,875 B2* | 1/2016 | Pan | A61B 6/06 |
| 9,259,191 B2* | 2/2016 | Noo | G21K 1/02 |
| 9,332,946 B2* | 5/2016 | Heuscher | A61B 6/405 |
| 9,339,252 B2* | 5/2016 | Sugihara | A61B 6/501 |
| 9,355,752 B2* | 5/2016 | Ohashi | H05G 1/02 |
| 9,357,971 B2* | 6/2016 | Yoshikawa | A61B 6/032 |
| 9,406,411 B2* | 8/2016 | Sayeh | G21K 1/04 |
| 9,462,985 B2* | 10/2016 | Hu | A61B 6/547 |
| 9,480,437 B2* | 11/2016 | Watanabe | A61B 6/022 |
| 9,566,040 B2* | 2/2017 | Hu | A61B 6/54 |
| 9,592,014 B2* | 3/2017 | Melman | A61B 6/06 |
| 9,627,098 B2* | 4/2017 | Ganguly | G21K 1/04 |
| 9,711,251 B2* | 7/2017 | Lee | G21K 1/04 |
| 9,808,209 B2* | 11/2017 | Wang | A61B 6/4078 |
| 9,820,709 B2* | 11/2017 | Melman | G21K 1/04 |
| 9,820,715 B2* | 11/2017 | Kang | A61B 6/542 |
| 9,848,840 B2* | 12/2017 | Ohashi | A61B 6/06 |
| 9,888,888 B2* | 2/2018 | Kobayashi | A61B 6/06 |
| 9,892,810 B2* | 2/2018 | Kwerreveld | G21K 1/046 |
| 9,931,087 B2* | 4/2018 | Melman | G21K 1/04 |
| 9,980,690 B2* | 5/2018 | Muroi | A61B 6/463 |
| 9,993,221 B2* | 6/2018 | Kim | A61B 6/547 |
| 9,997,269 B2* | 6/2018 | Roh | A61B 6/405 |
| 10,076,291 B2* | 9/2018 | Arai | A61B 6/06 |
| 10,085,706 B2* | 10/2018 | Kang | A61B 6/5211 |
| 10,123,756 B2* | 11/2018 | Karch | G21K 1/10 |
| 10,149,654 B2* | 12/2018 | Melman | A61B 6/06 |
| 10,176,601 B2* | 1/2019 | Morf | A61B 6/585 |
| 10,241,060 B2* | 3/2019 | Kim | A61B 6/06 |
| 10,314,553 B2* | 6/2019 | Ikhlef | A61B 6/032 |
| 10,327,717 B2* | 6/2019 | Melman | G21K 1/043 |
| 10,492,742 B2* | 12/2019 | Nakai | A61B 6/463 |
| 2004/0234034 A1 | 11/2004 | De Godzinsky | |
| 2007/0086576 A1 | 4/2007 | Yang | |
| 2014/0233707 A1 | 8/2014 | Grodzins | |

\* cited by examiner

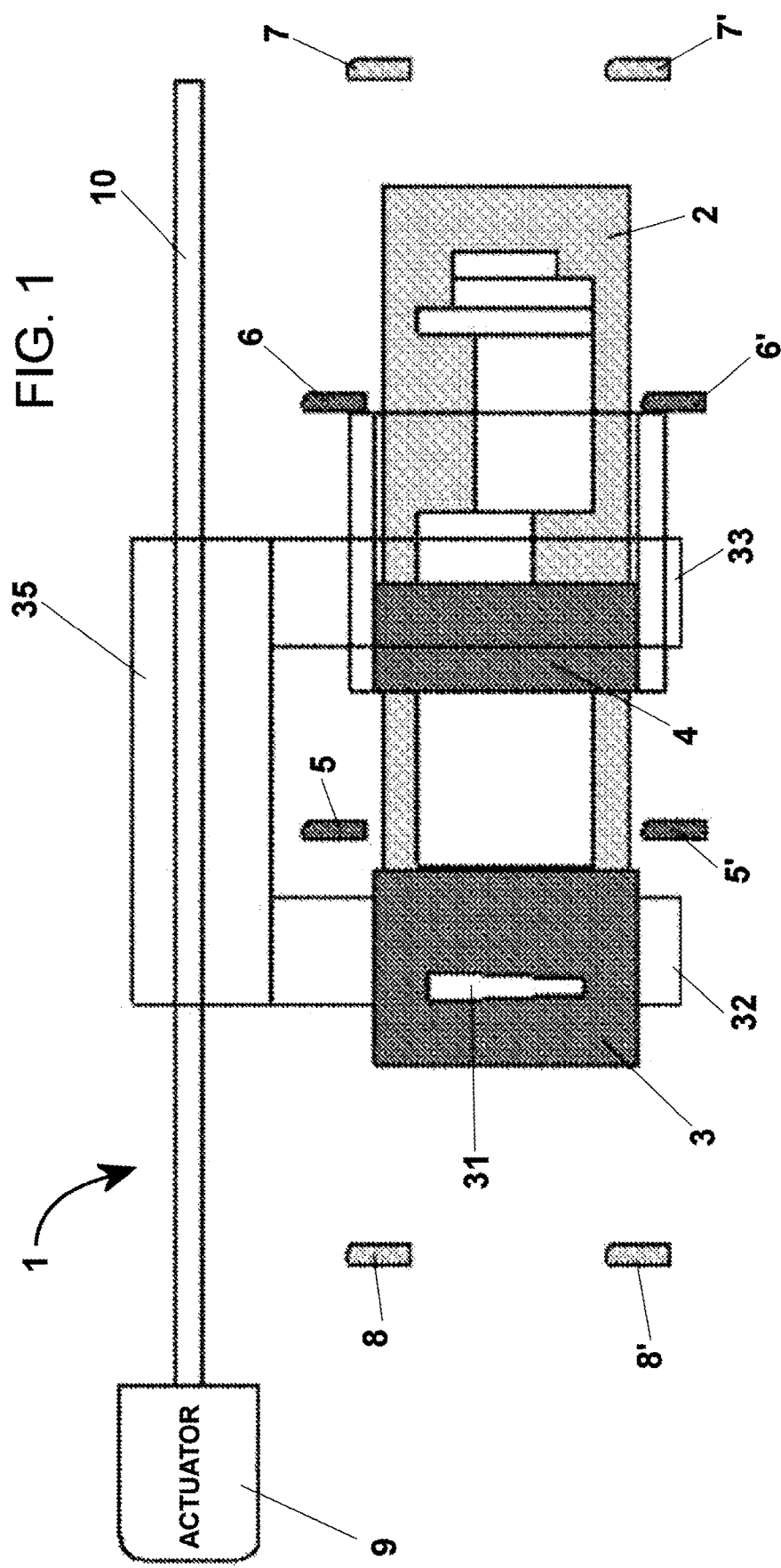

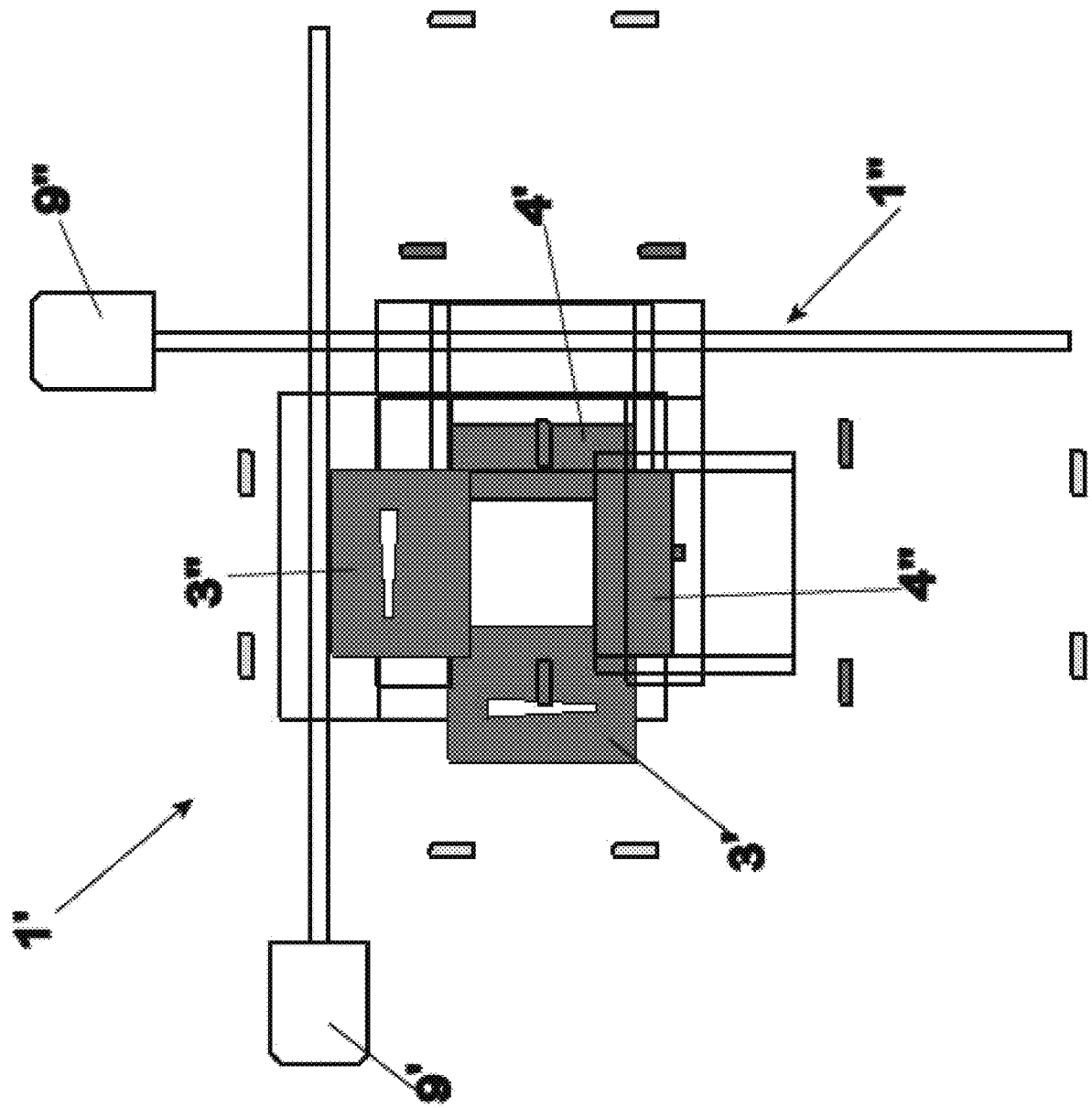

BEAM-LIMITING DEVICE FOR RADIOGRAPHIC APPARATUSES

FIELD OF THE INVENTION

The present invention relates to the technical field of radiography, and in particular to X-ray beam limiting devices used to define the shape of the X-ray bundle emitted by the radiogenic tube during radiograph acquisitions.

BACKGROUND OF THE INVENTION

In dentistry, different kinds of radiographic image acquisitions are known. Hereunder a brief description is provided of different types of acquisitions, to which reference will be later made.

Panoramic radiography (also known as orthopantomography, abbreviated as PAN) produces a radiographic image of a curved plan approximating patient jaws, with blurring of the anatomical structures laying outside a narrow layer around the predesigned curved plane. It is a planar radiography, to which reference will also be made as 2D.

Cone beam volumetric radiography (also known as CBCT or 3D) is the acquisition, from different projection angles, of a series of two-dimensional radiographic images, which will be processed post-acquisition to reconstruct three-dimensional volumes.

Teleradiography (abbreviated as CEPH) is a projective radiographic technique, producing radiographic images of the skull or of other anatomical areas from different projections, with minimum magnification and geometrical distortion. Usually two perspectives are represented, latero-lateral and antero-posterior.

During the acquisition of the different types of radiographic image (PAN or 2D; CBCT or 3D; CEPH), the radiogenic tube generally emits an X-ray bundle which is limited with shielding set near the X-ray source; the emitted X-ray bundle is generally conical or pyramidal. The X-ray bundle is then defined downstream the emission point through its passage through a window enabling to confer more precisely the desired shape and dimensions. Usually, with the passage through the beam-limiting device, the bundle section takes a quadratic or rectangular shape.

In the different kinds of radiographic acquisitions, windows having different shapes and dimensions are needed, which are interposed between the X-ray source and sensor, with the aim of conferring to the X-ray bundle the shape and dimensions optimal for that particular acquisition.

The use of X-ray beam limiting devices is well known in the art, and in particular the use of beam limiting devices making use of one or more blades which can be moved in different ways through suitable actuators. These beam-limiting devices are also called collimators.

Typically, a beam limiting device comprises two blades and one or two actuators moving them. In this way, a window having a fixed height (blades height) and variable width (the distance between the internal edges of the two blades) can be obtained. Known art documents describing devices built according to the above principles are e.g. EP1390956B1 and EP2139398A1 of Planmeca OY, and EP2642491A1 of the same applicant CEFLA.

EP1390956B1 describes a beam-limiting device wherein the actuator directly controls a single blade, while the other blades are moved with an indirect connection, so that the actuator can directly control the position of a blade only. In particular, in the case of inversion of the movement direction of the blade, the actuator controls at a maximum a blade only (the others remain fixed in the position in which they were at the moment of movement inversion).

Also EP2139398A1 works like EP1390956B1, even if instead of having two blades which approach and distance each other, there is a blade which approaches and withdraws and a punched plate for vertical collimation.

In EP2642491A1 the actuator can move two blades at the same time, even in case of inversion of movement direction, but the two blades move always in opposite direction one with respect to the other, with a modification of field width.

A feature of the known art described in EP1390956B1 and EP2642491A1 consists in the fact that the above-quoted collimators are formed by at least two blades and an actuator: if a quadratic window is desired (e.g. delimited on four sides) two collimators are needed, which are perpendicularly disposed, as shown e.g. in the FIG. 1 of EP1390956B1. This makes known art collimators quite expensive, in that two actuators are needed.

In the meanwhile, so-called hybrid extraoral apparatuses have become commonplace, capable of acquiring 2D PAN images, needing a fan beam, and 3D CBCT images, needing a pyramidal beam. This requires the collimator to assume a split shape (a long, thin rectangle) and a quadratic form of different dimensions.

Normally extraoral radiographic apparatuses enable the acquisition of complete dental arches; nonetheless often dentists need to acquire a well-defined region of interest (e.g. a molar tooth area) having dimensions smaller than the complete dental arch. That is, a sub-volume is to be acquired, which can be not centered on the rotation axis of the apparatus. The acquisition of an area having smaller dimensions allows giving a smaller dose of X-rays to a patient. In this case, normally said patient is moved inside the radiographic apparatus in an asymmetrical position, so as to position the region of interest in a central position with respect to the rotation axis of the radiographic apparatus.

SUMMARY OF THE INVENTION

Aim of the present invention is providing a beam-limiting unit capable of producing a window having the desired width and the shape. Moreover, is also aim of the present invention providing a beam-limiting unit capable of setting in a short time; reducing the number of electronically moved components, the beam-limiting unit is more reliable and easier to control, and of cheap production.

The aim of the invention is obtained with the beam limiting devices according to the present invention, wherein different embodiments are present:

first embodiment: two perpendicularly set overlapping beam limiting units having each two blades to obtain both vertical and horizontal collimation;

second embodiment: only one planar limiting unit, wherein three elements are present: a punched plate for vertical collimation and two blades which can be approached and withdrawn to each other for horizontal collimation; overall only one actuator is present;

third embodiment: only one cylindrical limiting unit, wherein three elements are present: a punched plate for vertical collimation and two blades which can be approached and withdrawn to each other for horizontal collimation; overall only one actuator is present.

The cylindrical embodiment is less bulky, even if is more difficult to design.

The beam-limiting unit according to the present invention is different from the above-quoted known art in that the actuator controls all the blades, and anyway at least two blades, in a direct way and in both directions, so that the outbound X-ray bundle remains substantially of steady dimensions, even if the limiting unit itself is moved during an acquisition.

The collimators according to the present invention have several advantages.

A first advantage consists in obtaining a collimator that is particularly cheap to produce, in that it uses one actuator only.

A second advantage consists in obtaining a collimator that can be mounted on hybrid apparatuses, capable of acquiring 2D and 3D images.

A third advantage consists in having a collimator that enables acquiring small regions of interest, not coaxial to the rotation axis of the apparatus, while giving the patient a minimal dose of X-rays, without the need of modifying the positioning of the patient in the apparatus.

BRIEF DESCRIPTION OF THE DRAWINGS

Further advantages and properties of the present invention are disclosed in the following description, in which exemplary embodiments of the present invention are explained in detail based on the drawings:

FIG. 1 is a front view of a planar collimator according to the invention;

FIG. 2 is a top view of the planar collimator;

FIG. 70 shows a collimation sequence: initial position of the planar collimator in front view;

FIG. 8 illustrates two overlapping planar collimators set perpendicularly, in front view;

DETAILED DESCRIPTION OF EMBODIMENTS OF THE INVENTION

Figure 3:
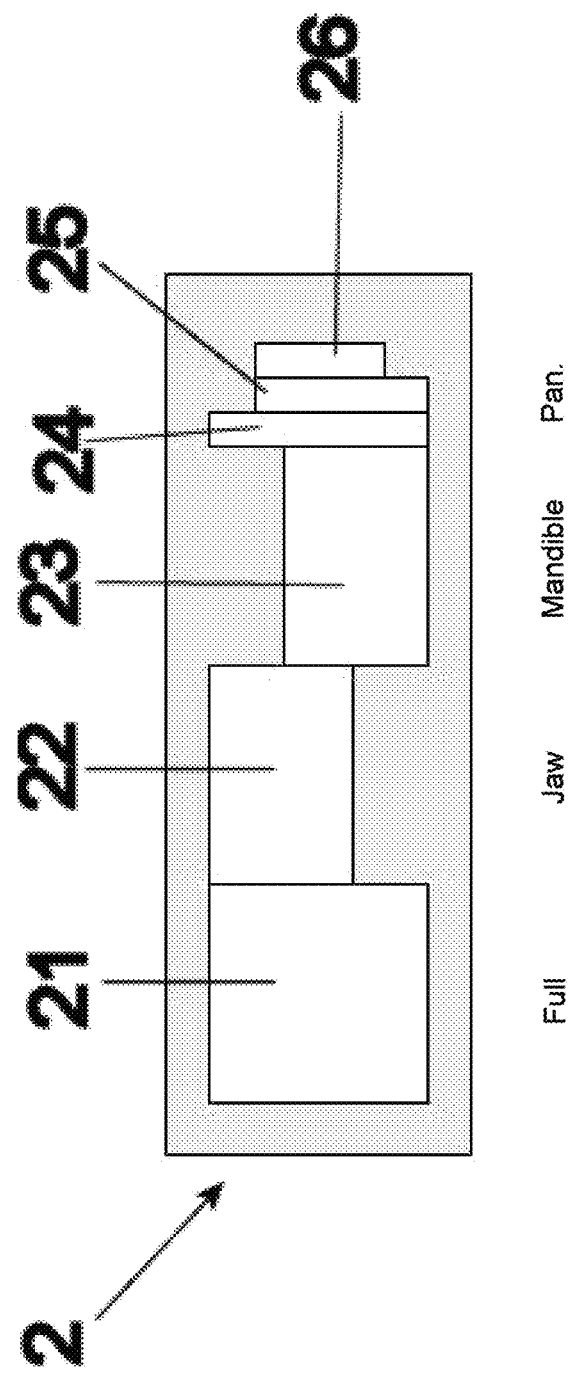
FIG. 3 illustrates details of a punched plate.

With reference to the figures, it is known to a person of skill in the art that that blades and a punched plate for this kind of apparatus are to be made of a material capable of stopping X-rays, such as lead.

The beam limiting device 1 or 11 or 1'-1" must be arranged immediately downstream of the X-ray source (not shown). The X-ray bundle of substantially conical shape passes through the beam-limiting device 1 or 11 or 1'-1" and its shape is modified.

Both embodiments of the beam-limiting device described herein are based on the same mechanical principles; nonetheless, understanding the functioning of the device in its planar form is easier. The planar form will therefore be described first. The cylindrical collimator can be considered as a cylindrical rolling of the different planar figures.

The beam-limiting device, or collimator, may have a planar form to define a planar beam-limiting device 1, which comprises two blades 3 and 4, which can be approached to or withdrawn from each other to vary the width of the X-ray bundle (horizontal collimation). The sliding of the blades 3 and 4 is caused by a unique actuator 9.

In front of or behind the blades 3 and 4 there is a punched plate 2, which in its turn comprises a plurality of windows 21-26 of different dimensions, both in height and width. The unique actuator 9 causes the motion of the punched plate 2, too, in order to bring the desired window in front of the X-ray bundle. This allows setting the height of the X-ray bundle (vertical collimation).

FIG. 2 shows a possible configuration of the planar collimator 1, wherein the blade 3 and the blade 4 are arranged on the same side of the punched plate 2, in front or behind it with respect to X-ray path. Nonetheless, it is possible that the blades 3 and 4 are on the opposed sides of the punched plate 2. The action of friction devices 15 is represented with dotted lines (see below).

The final form of the collimated X-ray bundle results from the respective disposition of the punched plate 2 and of the blades 3 and 4.

E.g., in the configuration shown in FIG. 1, the X-ray bundle is collimated to acquire a 3D image, and substantially passes through the window 21 without being limited by blades 3 and 4. On the other hand, would blades 3 and 4 approach, superimposing them to window 21, a fan beam is obtained. A further way to obtain a fan beam for a PAN acquisition is sliding the blade 3 so as to bring the V-window 31 in correspondence with the (not shown) central point of the X-ray bundle. It is worth noting that in FIG. 1 the window for the PAN acquisition is represented having a V-form, while it is possible to acquire a PAN image using a window having a rectangular shape.

Figure 4:
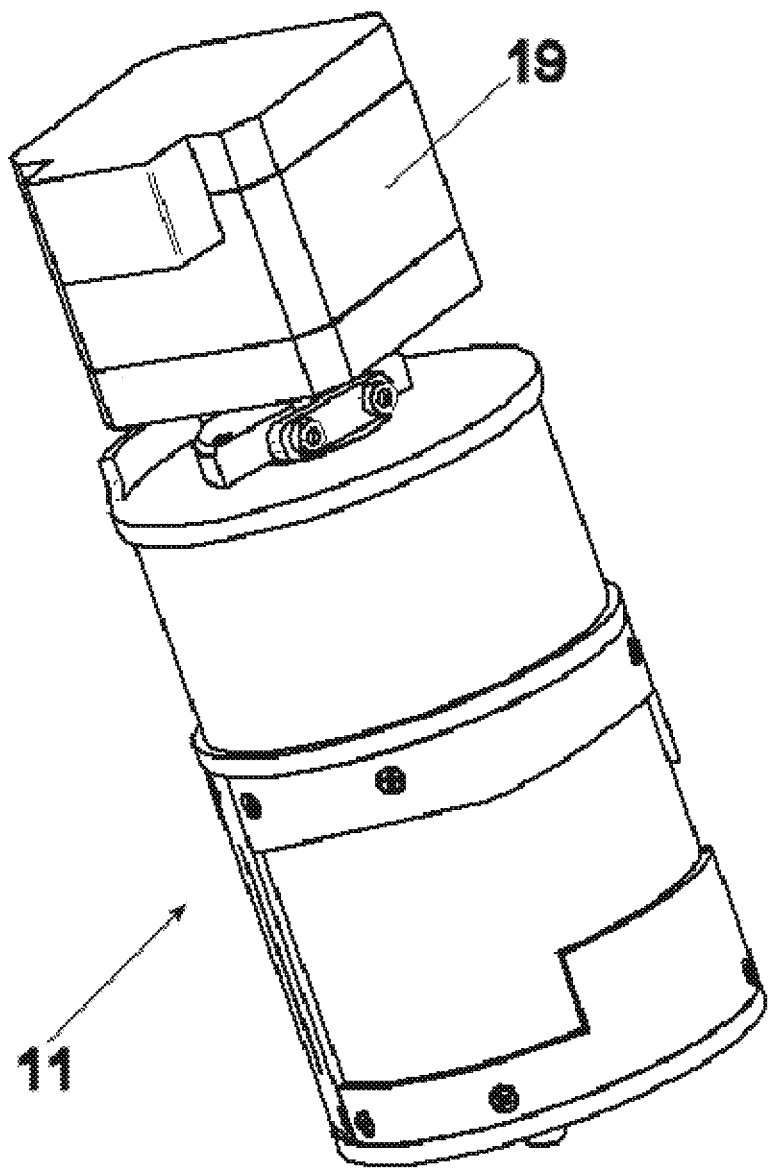
FIG. 4 is an axonometric view of a cylindrical collimator according to the invention.

FIG. 4 shows an axonometric view of the beam-limiting device in its cylindrical embodiment, which defines a circular beam-limiting device 11. In this embodiment, too, only one actuator 19 is present.

The working principle of the circular beam-limiting device 11 is the same illustrated for the planar beam-limiting device 1.

Figure 5:
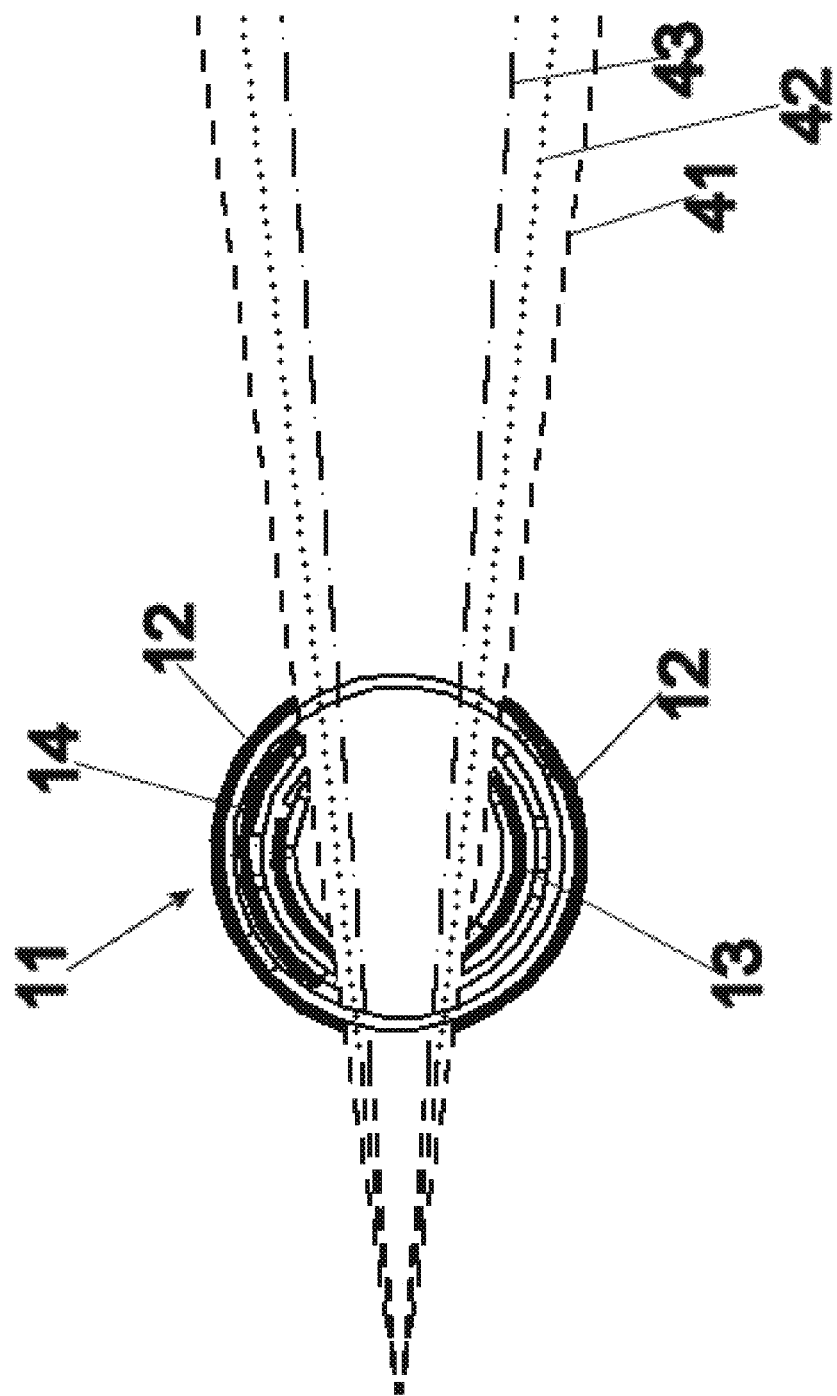
FIG. 5 is a transversal section of the cylindrical collimator.

FIG. 5 shows a transversal section of the cylindrical device 11. The outer cylinder 12 is the punched plate 2 rolled in a cylinder, with windows that are equivalent to the windows 21-26 already seen in FIG. 3. As in the planar collimator 1, said windows set the vertical collimation of X-ray bundle. Inside the outer cylinder 12, two cylindrical blades 13 and 14 slide. They can be approached or withdrawn to each other thanks to the action of an actuator 19, so defining the window in the horizontal direction (horizontal collimation). The outer cylinder 12 is rotated by the actuator 19, too, bringing in front of the X-ray bundle the window desired in that moment.

It is quite intuitive that, sliding the two cylindrical blades 13 and 14, the width of the X-ray bundle can vary from the wider bundle 41 to an intermediate width 42, to an even more restricted width 43.

The very marked thickness of the outer cylinder 12 and of the two cylindrical blades 13 and 14 aims to show the presence of lead, which is notoriously radio-opaque and therefore blocks the X-ray path.

Figure 6:
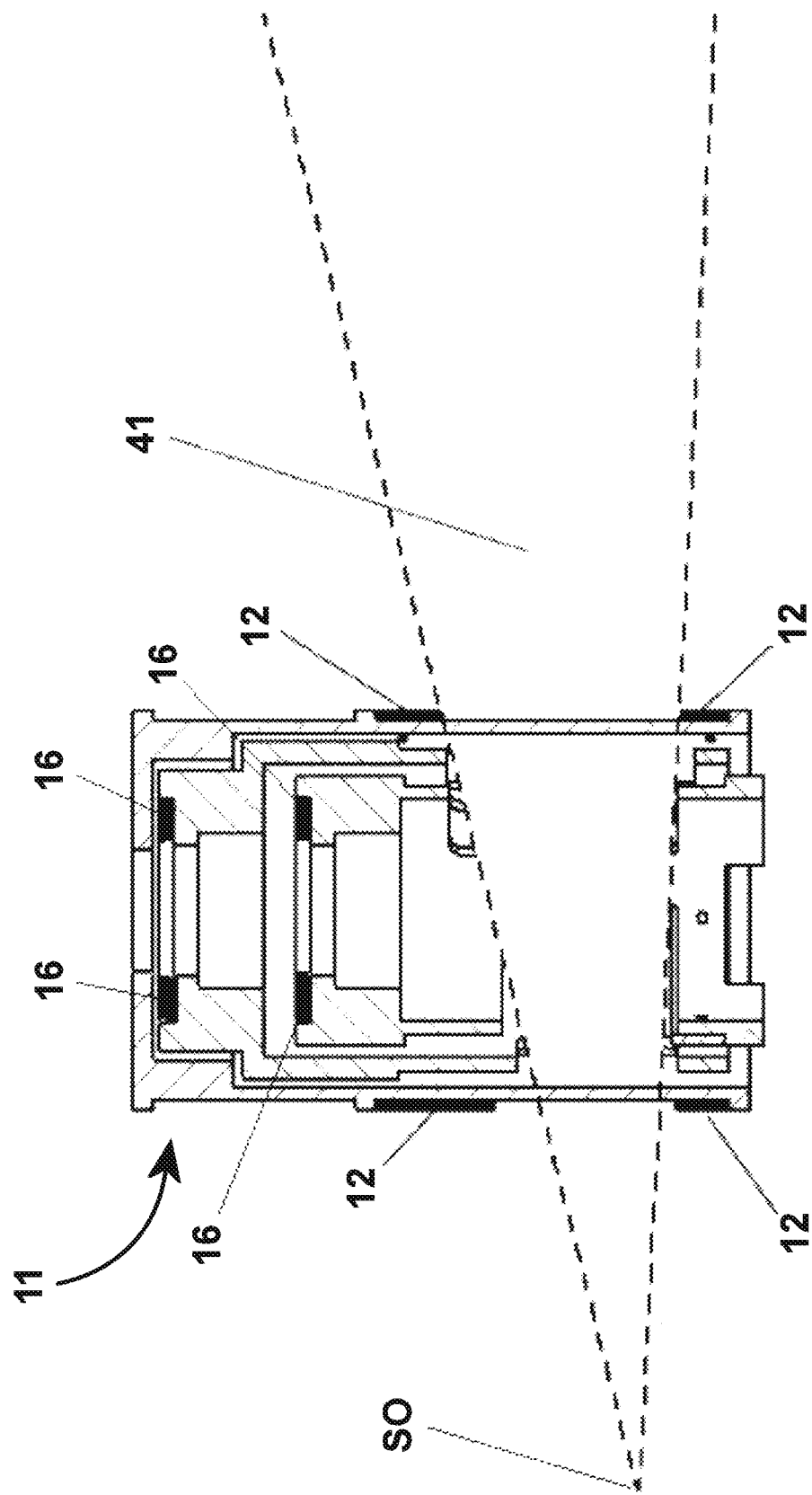
FIG. 6 is a longitudinal section of the cylindrical collimator.

In order to obtain a very precise collimation for PAN acquisitions, in a preferred embodiment on the outer cylinder 12 a very thin window is present, which is used alone, without the need of further collimation by two cylindrical blades 13 and 14. FIG. 6 is a longitudinal section of the cylindrical collimator 11, which shows how the cylindrical collimator 11 vertically limits the X-ray bundle (dotted lines) coming out from the (not shown) X-ray source. In the section only the punched plate 12 can be observed, while the two cylindrical blades 13 and 14 are not lying on the section plane and therefore are not visible.

The way in which the different configurations are obtained is similar both for the planar collimator 1 and for the cylindrical collimator 11. Again, the planar collimator 1 will be explained first, in that it is more intuitive.

As shown in FIG. 1, in the case of the planar device, the blades 3, 4 for (variable) horizontal collimation and the punched plate 2 (vertical collimation; fixed windows) are supported on a unique carriage 35 dragged by a screw 10, in its turn activated by the actuator 9.

The carriage 35 supports a fork having two prongs 32, 33, the fork having an aperture equal to the needed maximal horizontal width of blades 3, 4.

In the following description, one of the blades 3, 4 for the horizontal collimation is integral to its prong, while the other blade (4 or 3) is connected to the prong through a friction device 15; the punched plate 2 is connected to the prong through a friction device, too. An alternative configuration is possible, wherein the punched plate 2 is fixed, while the two blades 3, 4 for the horizontal collimation are connected to the other prong through a friction device.

It is apparent that the fact that blade constraint is on the right or left has no influence; in the present example, the constraint is described on the left side, but the specular configuration is possible. For simplicity's sake, in the following reference will be made in which the blade 3 is integral to the fork's prong 32, while the blade 4 and the punched plate 2 are fixed on the other fork's prong, each with its own friction device, respectively.

In an embodiment, the fixed blade can also have a window 31, which is used for collimating during panoramic acquisitions.

The punched plate 2 has two couples of end of stroke, end of stroke 8, 8' placed on the left, and the end of stroke 7, 7' placed on the right of FIG. 7.

The blade 3 has only the (not shown) end of stroke of carriage 35.

The blade 4 has the end of stroke 5, 5' placed on the left, and 6, 6' placed on the right of FIG. 7.

According to the last image acquisition, the collimator 1 or 11 or 1'-1" will be in a given position when a new setting for the following acquisition is needed. From that position, the collimator 1 or 11 or 1'-1" is brought to an initial position 0, from which the setting for the next acquisition is started.

To describe the functioning of the collimator 1, several figures will be used, which have to be considered in sequence. For simplicity's sake, let us say that the initial position 0 of the collimator 1 is the situation shown in FIG. 7D.

Figure 7O:
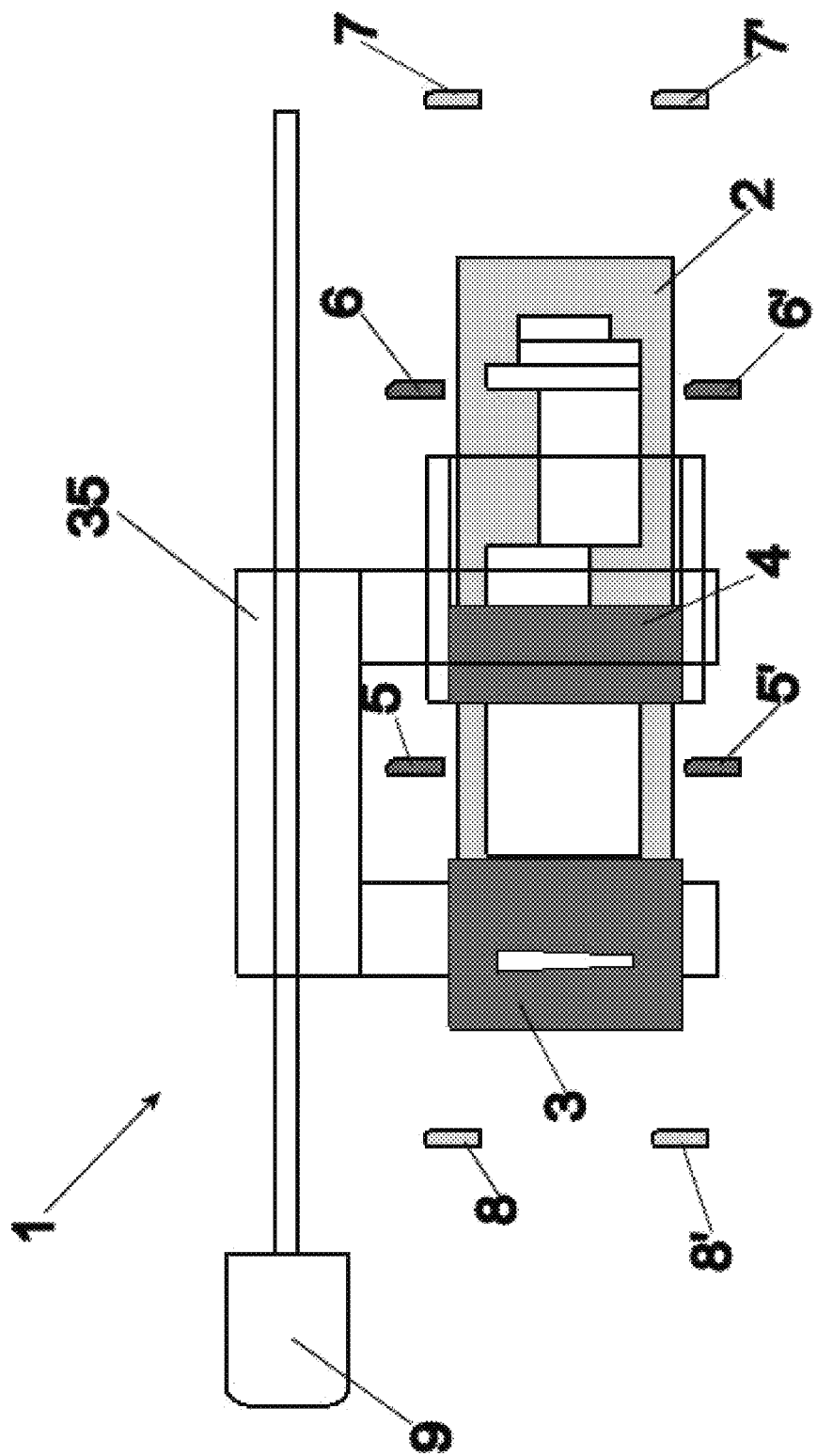
FIG. 7A shows a collimation sequence: first position of the planar collimator in front view.
FIG. 7B shows a collimation sequence: second position of the planar collimator in front view.
FIG. 7C shows a collimation sequence: third position of the planar collimator in front view.
FIG. 7D shows a collimation sequence: final position of the planar collimator in front view.
Figure 7A:
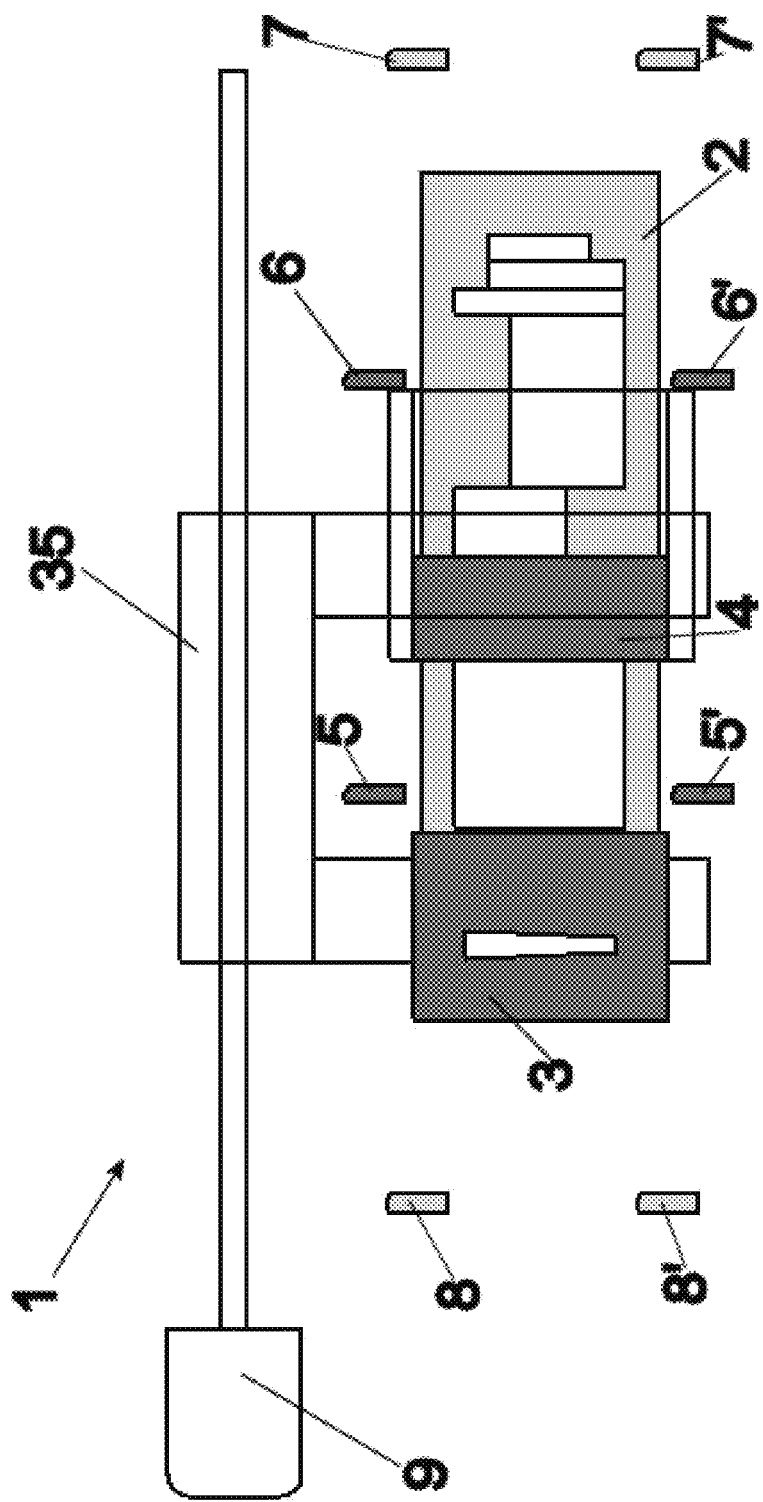

Now the actuator 9 moves the carriage 35 towards the right, up to the point when the blade 4 bumps into the end of stroke 6, 6' stopping, as shown in FIG. 7A.

Figure 7B:
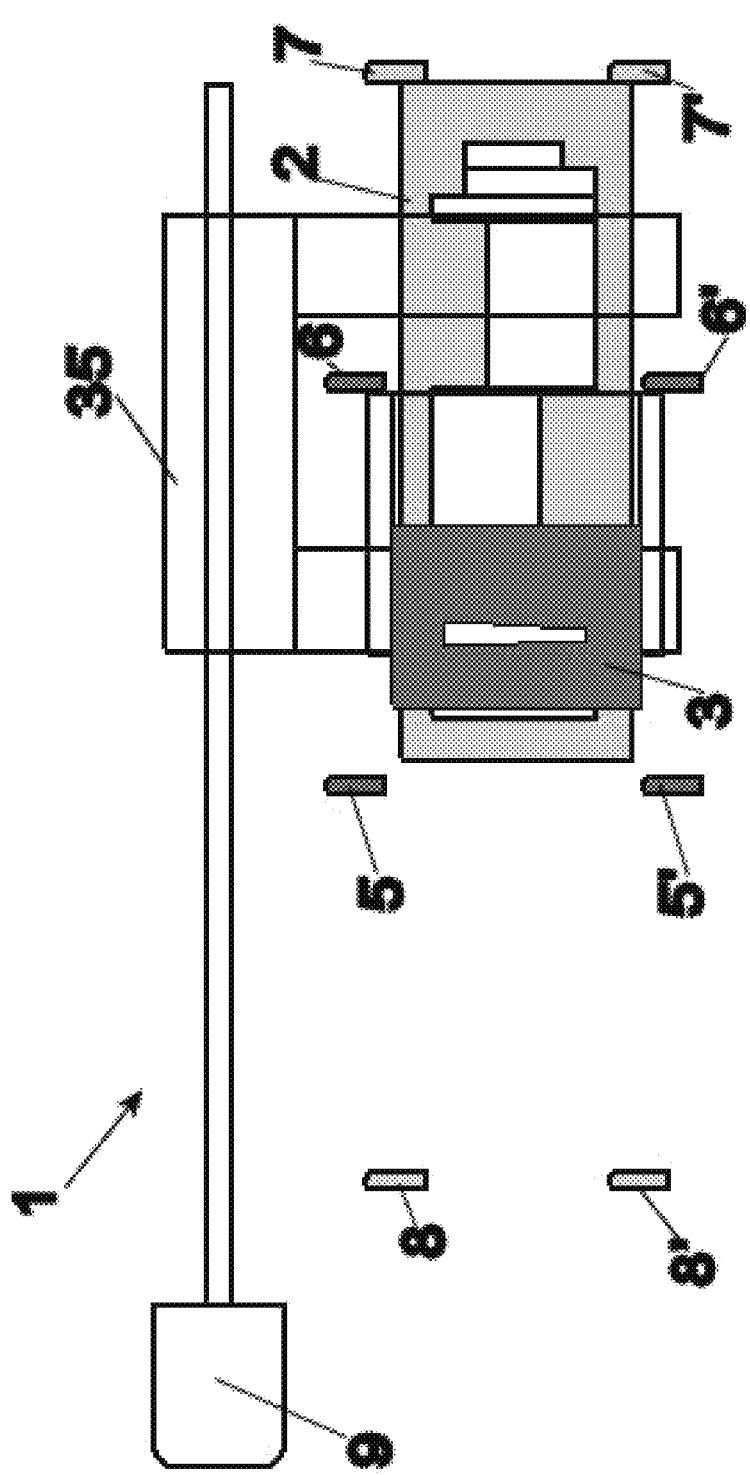

The blade 3 and the punched plate 2 continue to move integrally with the carriage 35. The movement continues until also the punched plate 2 bumps into the end of stroke 7, 7' stopping. The blade 3 continues to move integrally with the carriage 35 until it reaches the position needed for the desired acquisition with respect to the punched plate 2, as shown in FIG. 7B. It is worth noting that the blade 3 completely superimposes to the blade 4, which is therefore not visible in FIG. 7B. The relative position of the blade 3 and of the punched plate 2 remains fixed until the end of the setting of the collimator 1.

Figure 7C:
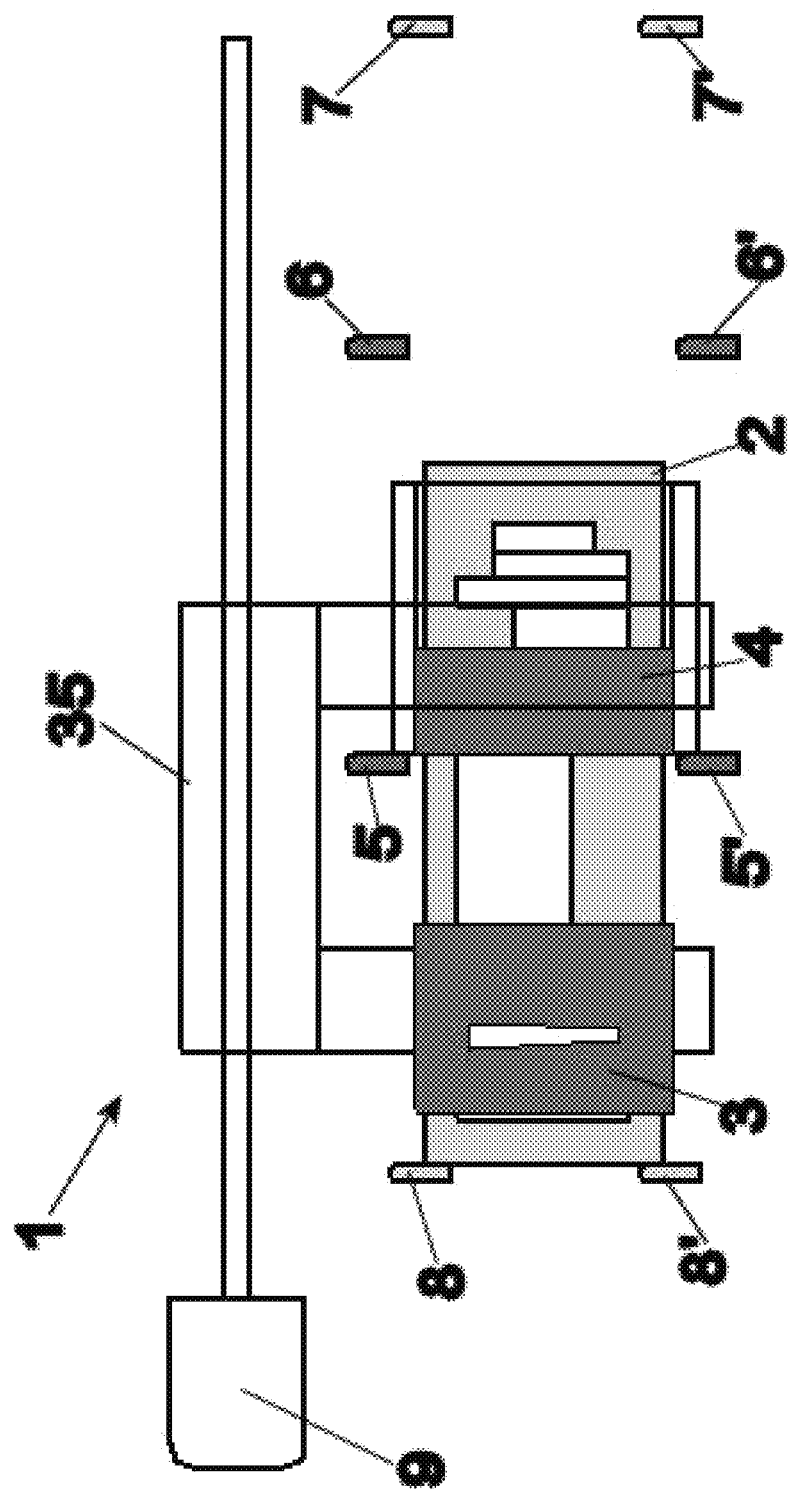

Now the carriage 35 moves towards the left until the blade 4 bumps into the end of stroke 5, 5' stopping. The blade 3 and the punched plate 2 continue to move towards the left, until the blade 3 reaches the desired aperture with respect to the blade 4, as shown in FIG. 7C. The relative position between blades 3 and 4 and the punched plate 2 is fixed until the end of the setting.

Figure 7D:
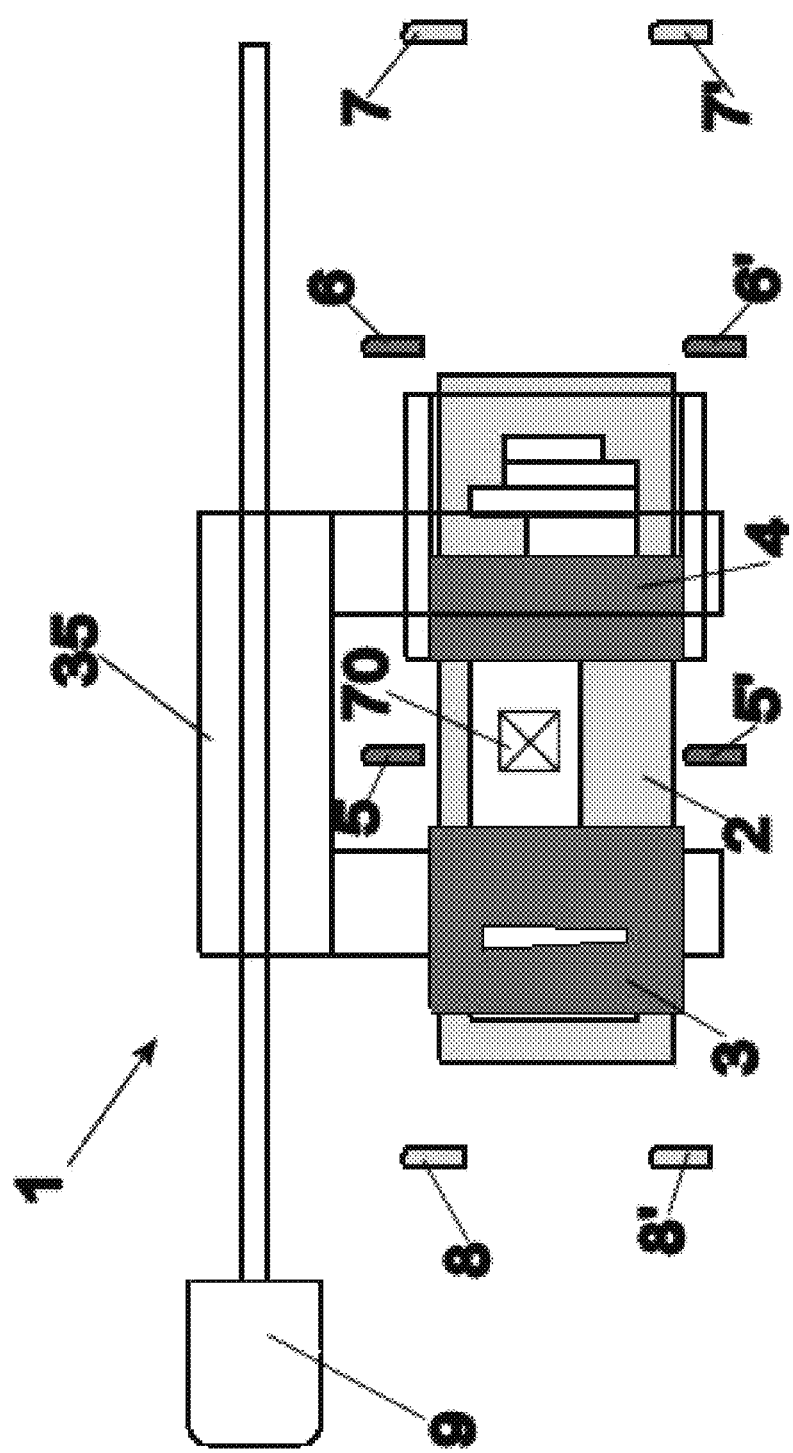

Now the integral assembly of punched plate 2 and blades 3, 4 is dragged towards the right to be placed precisely in front of the X-ray source, so that the central X-ray 70 of the X-ray bundle is at the crossing of the diagonals of the window that has formed, as shown in FIG. 7D.

A (not shown) filter can be integral to the fixed blade so as to be inserted only for CBCT acquisitions.

An alternative embodiment to obtain a planar beam-limiting device 1 consists in removing the punched plate 2 and superimposing two perpendicularly set beam-limiting units 1' and 1", as shown in FIG. 8. In order not to complicate too much the figure, neither the end of stroke nor the carriages were numbered. In this way, the aperture between the blades 3' and 4' and between the blades 3" and 4" allows collimating both vertically and horizontally. Nonetheless, in this case two actuators 9' and 9" will be needed, which is a drawback. On the other hand, in this way no limits are set to the vertical collimation, which can be as wide as desired, inside the limits allowed by the blades 3" and 4".

Figure 9:
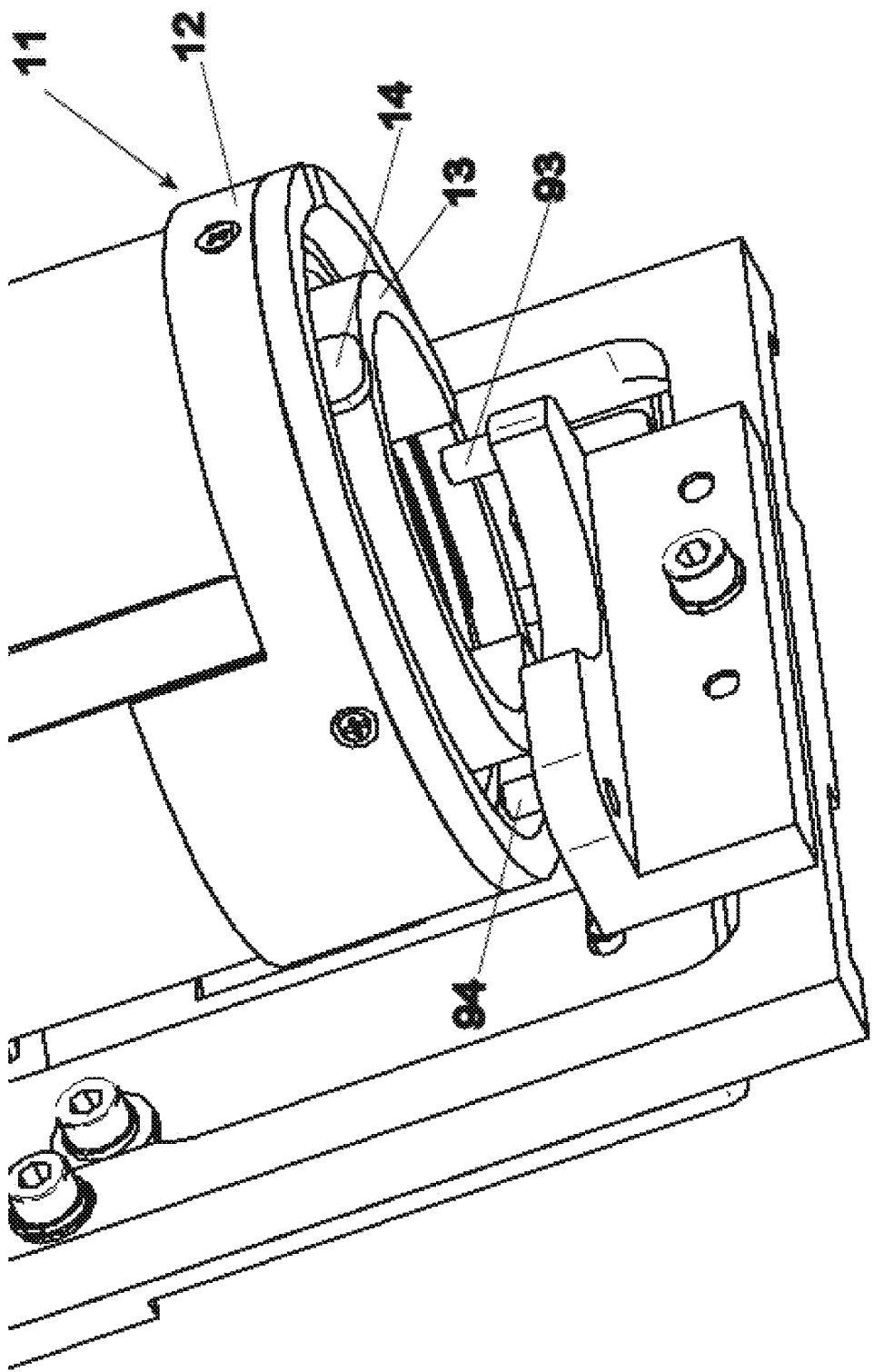
FIG. 9 illustrates a magnified detail of the bottom part of the cylindrical collimator in axonometric view.

As already mentioned, the functioning of the collimator in its cylindrical embodiment 11 is very similar to the functioning of the collimator in the planar form 1. Here, too, as shown in FIG. 9, two end of stroke 93 and 94 are present, which limit the rotation of the cylinders 13, and 14, respectively. Said end of stroke are in the form of a pin. On the other hand, the cylinder 12, corresponding to the punched plate 2, is free to rotate over 360°, and is free from end of stroke (it can rotate indefinitely, both clock-wise and anti-clockwise, observing it from top).

Between the cylinder 14, corresponding to the blade 4, and the cylinder 12, corresponding to the punched plate 2, there is a friction device 16; similarly, there is a friction device between the cylinder 13, corresponding to the blade 3, and the cylinder 14, corresponding to the blade 4. The three cylinders 12, 13, 14, move at the same time thanks to the presence of (not shown) friction devices until one of them (13, or 14, or 13 and 14) bumps into its respective end of stroke (93, 94). As a consequence, through a precise sequence of clockwise and anti-clockwise rotations of determined angles, the three cylinders 12, 13, 14 can be placed at desired angular coordinates. This allows collimating the X-ray bundle both in the vertical direction (thanks to the windows in the cylindrical punched plate 12) and in the horizontal direction (thanks to the respective opening-closing of the two cylinders 13 and 14).

As explained above, the mechanical connection of the first blade, actioned by the actuator, with the second blade occurs through a friction device.

In the cylindrical collimator, the connecting friction device is realized through a circular wave spring (but a spiral spring could be used, too), capable of providing a well-determined axial thrust. This axial thrust acts on a disc made of sliding material, connected to the first blade/actuator, in our case made of plastic material, coupled with another suitable material connected with the first blade, in our case made of aluminum, so that motion can be transmitted up to a limit given torque. Once the limit torque is exceeded, the two surfaces detach, and the friction device slides. The sliding material limits the wear during the sliding phase. This occurs when the second element reaches the mechanical end of stroke.

In the planar collimator, the same device is realized through two planar elements in contact; at least one of the two materials must be sliding. The two elements are kept united one above the other applying a given transversal thrust. This thrust in this case is obtained through two pressurizing springs in the transversal direction. Applying a longitudinal thrust between the two elements, they will remain united until a maximal detachment thrust is exceeded. Once this thrust is exceeded, a longitudinal sliding between the two elements will occur. This occurs when the actuator acts on the first element and the second reaches the mechanical end of stroke.

One of the advantages of the collimator according to the present invention consists in allowing the irradiation of a reduced area of a dental arch, allowing the acquisition of a more restricted area with respect to the complete dental arch, giving a lower X-ray dose to the patient. Let us suppose, e.g., that the point on which the dentist has to intervene is the area of the upper right molar.

In this case, the patient is positioned inside the extraoral radiographic apparatus using always the same patient positioning device, and placing the patient always in the same way inside it, symmetrically with respect to the rotation axis of the apparatus. Thanks to the collimator according to the present invention, irradiating only a small area around the concerned molar, is possible, as shown in FIG. 10.

In the acquisition of the complete dental arches, the X-ray bundle collimated by the collimator 11 allows the acquisition of the entire volume Z.

Figure 10:
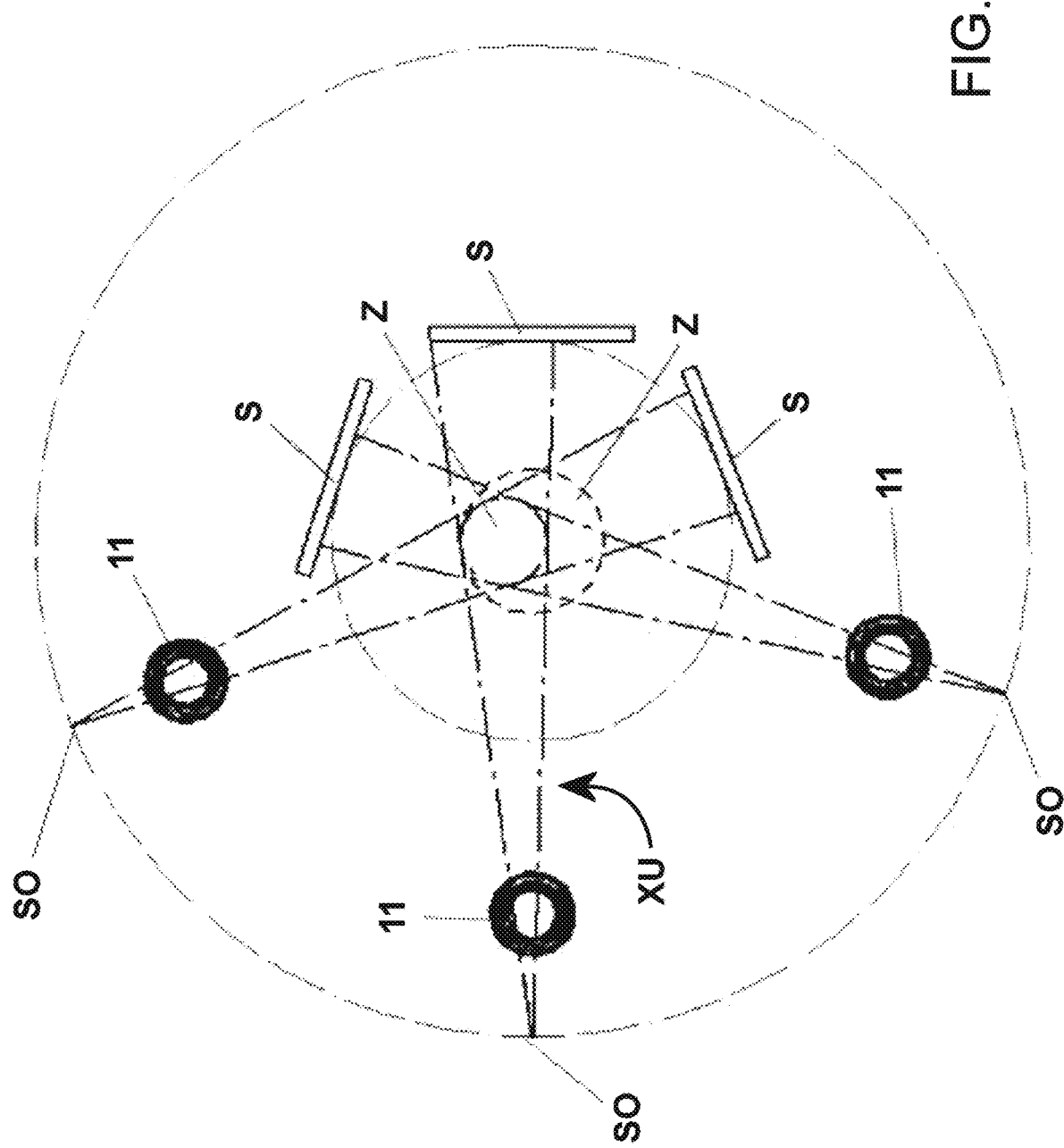
FIG. 10 is a top view of the acquisition of a sub-volume (sub-volume not cantered on the rotation axis of the apparatus)

In another kind of acquisition, the collimated X-ray bundle through the collimator 1 or 11 allows acquiring a volume z smaller than the complete arch, and placed in asymmetrical way with respect to the sagittal plane of the patient, as can be observed in FIG. 10. This is possible thanks to the fact that, once set the respective disposition of blades 2, 3, 4, or cylinders 12, 13, 14, that disposition is kept integral, while the integral assembly of blades 2, 3, 4 cylinders 12, 13, 14 pivots in order to irradiate always the volume z only during the rotation of the X-ray source and sensor (S). The process of acquisition of a reduced region of interest is shown in FIG. 10.

It hardly needs be mentioned that the movement of integral rotation of the three blades 2, 3, 4 or cylinders 12, 13, 14 must be synchronized with the rotation movement of the X-ray source (SO) and sensor—(S) around the patient (z, Z).

Figure 11:
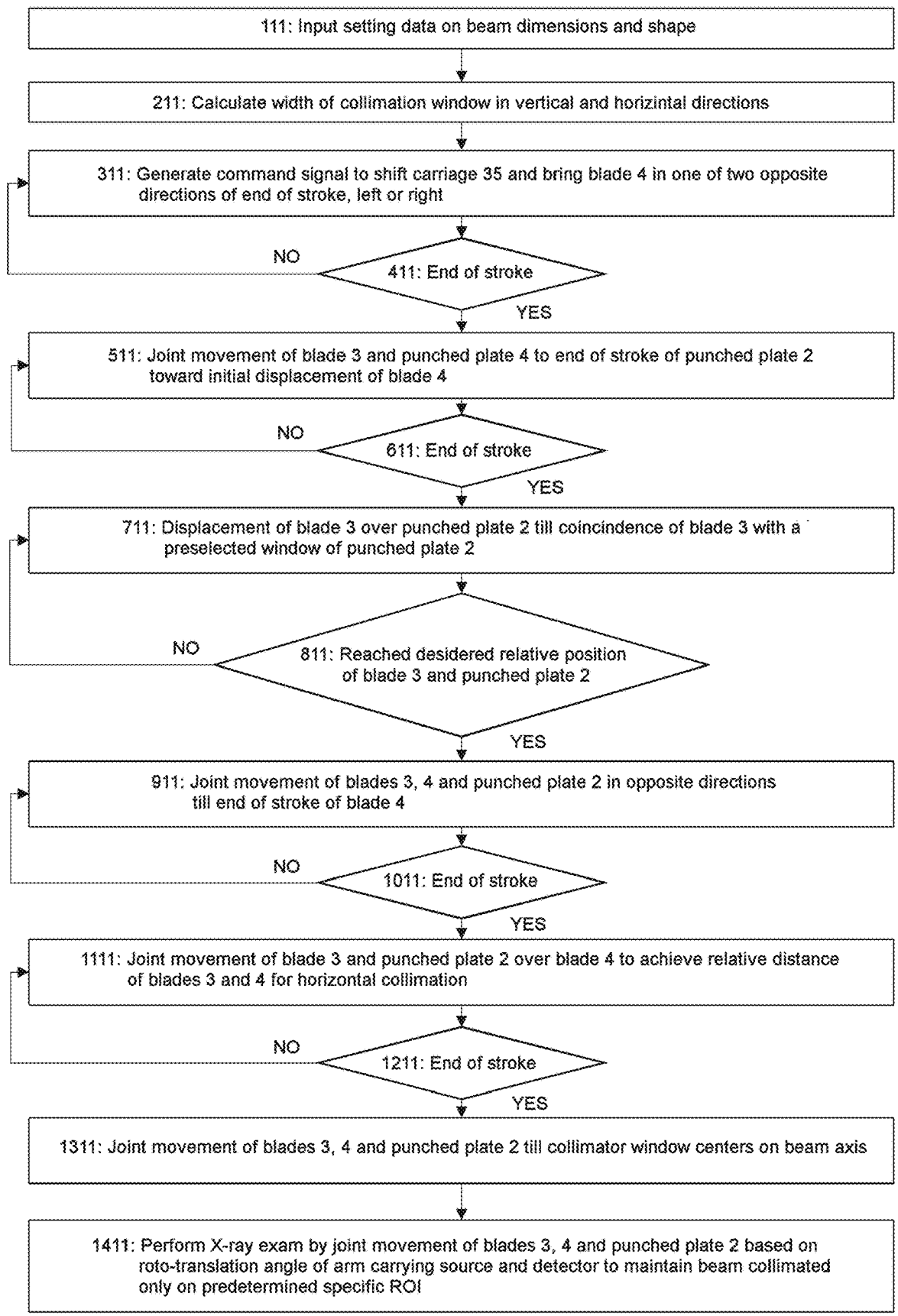
FIG. 11 is a flowchart of an example of a setting sequence of the collimator according to the present invention.

FIG. 11 is a flowchart showing an example of a sequence for setting the collimator according to the present invention.

At step 111, using a man-machine interface with the control system of the collimator, the setting data of the desired X-ray bundle are inputted. These data can be known by human operators, or can be derived by tables indicating typical values according to the acquisition, or alternatively can be automatically determined by the control system in consequence of the inputting of the image to be acquired, or kind of scanning and anatomical area to be acquired, i.e. one or more regions of one or two dental arches.

The control system, which can be any unit provided with a processor and/or an electronic circuit capable of performing pre-set operations, calculates the vertical and horizontal width and the shape of the X-ray bundle according to the data inputted at step 111, as indicated in step 211.

According to these values, at step 311 a first command signal of the actuator translating the blades 3, 4, and, if present, the punched plate 2, is sent to the actuator which shifts the carriage 35 towards anyone of two opposed positions of end of stroke of blade 4. Once the reaching of this condition is verified at step 411, passing to step 511 is possible; if not, the translation of the blade 4 is continued.

Once the blade 4 reaches the end of stroke position, a translation command of the blade 3 and of the punched plate 2 is generated, in the same direction of blade 4. In this case, the actuating command of the motor remains active even after the blade 4 has reached its end of stroke position.

In this position, the thrust of the motor on the blade 3 and on the punched plate 2 exceed the friction thrust dynamically connecting the blade 3 and the punched plate 2 to the blade 4, and those can continue their translation until the punched plate 2 reaches an end of stroke at step 511.

If said position is reached, then at step 611 the punched plate stops, while the blade 3 can be further translated with respect to the punched plate 2 and the blade 4, up to the reaching of a position of the punched plate 2 corresponding to a window of the punched plate itself, having the desired vertical width, of the same value of the desired bundle shape.

Once this position is reached and verified at step 811, all the blades 3, 4 and the punched plate 2 are shifted in 911 in a direction opposed to that of the end of stroke, until the reaching, by plate 4, of an end of stroke position opposed to the starting position. Once the position of end of stroke is reached and verified at step 1011, similarly to what was described for the preceding steps, the blade 3 and the punched plate 2 are further translated with respect to the blade 4 as described in 1111, and as long as the blade 3 is at a distance from blade 4 corresponding to the desired horizontal width of the collimator. Once this condition has been verified at step 1211, the collimator window is set with the desired shape, and the desired horizontal and vertical width corresponding to the desired X-ray bundle shape.

The assembly of the two blades 3, 4 and of the punched plate 2 is shifted at step 1311 to center the collimator window with the central axis of the X-ray bundle. Once the two centers are in phase, image acquisition can start.

As indicated at step 1411, when panoramic images or tomographic images have to be acquired, the X-ray source and sensor are rotated around the patient, with a pre-set roto-translatory movement of the rigid support arm of the X-ray source and sensor. Then it is possible that the area on which the X-ray impinge remains limited to a partial area of the dental arches corresponding to the region of interest of the acquisition, like a particular tooth or group of teeth, rotating the assembly of the blades 3 and 4 and of the punched plate 2 correspondingly to the roto-translatory movement of the arm.

In order to be able to carry out such limitation of the beam aperture so to irradiate a limited region of interest in the device according the above description the stops 5, 5'; 6, 6' respectively of the plane and of the cylindrical embodiments are positioned within the two opposite ends of the path of the first blade 3, 3', 3", 13. The said stops 5, 5'; 6, 6' are placed at a distance one from the other defining a path of displacement for the second blade 4, 4', 4", 14 which is shorter that the path of displacement of the first blade 3, 3', 3", 13 and which paths corresponds to a portion of the whole path of displacement of the said first blade. During the displacement along the said portion of path the first blade and the second blade are displaced together without changing their relative position in the direction of displacement. The said direction of displacement is in this case the direction perpendicular to a common axis of roto-translation of an X-ray unit (XU) comprising a source (SO) and a sensor (S) positioned on opposite sides of target to be limited.

Following the above construction of the device a method for limiting an X-ray is provided, wherein the set of a first and a second blades 3, 3', 3", 13; 4, 4', 4", 14 are displaced along a direction perpendicular to an axis of rotation of an X-ray unit comprising a source (SO) and a sensor (S) provided on opposite directions of an object to be imaged. The said first blade 3, 3', 3", 13, moves together with the said second blade 4, 4', 4", 14 maintaining a fixed reciprocal distance one from the other along a portion of the path of displacement of the first blade while translating the aperture for passing of the x-ray relatively to the axis of propagation of the said x-ray beam.

According to a further improvement the said common displacement of the first and second blades is carried out by synchronizing the displacement with the roto-translational movement of an x ray group comprising a source and a sensor (S) positioned on opposite sides of an object to be scanned.

According to an embodiment, the present invention is applied in an X-ray imaging device comprising at least an X-ray source and at least a sensor (S) which are mounted at two ends of an arm. The arm is rotating around an axis of rotation and the axis of rotation can be displaced in a plane perpendicular to it. An object to be scanned is placed between the x-ray source and the sensor (S). A unit comprising a processor configured to execute a control program for controlling the rotation of the arm and the displacement of the axis of rotation is provided this control unit controls also in a synchronized manner the common displacement of the two blades 3, 4 during the displacement along the path defined by the stops 5, 6 cooperating with the second blade 4. A synchronization unit reads the trajectories of the source and of the sensor and displaces the two blades correspondingly in order to irradiate a certain target region.

A further processing unit comprising a processor configured to receive the collected signals by the sensor and to generate image data out of them is provided which then send the image data to an image processor for generating and displaying the image corresponding to the received signals.

LISTING OF REFERENCE NUMBERS 1, 1'-1" Planar beam limiting device
11 Circular beam limiting device
2, 12 Punched plate
3, 3', 3", 13 First blade
4, 4', 4", 14 Second blade
5, 5' End of stroke
6, 6' End of stroke
7, 7' End of stroke
8,8' End of stroke
9, 19 Actuator
10 Screw
15, 16 Friction device
21-26 Windows
31 V-shaped window
32 Left prong
33 Right prong
35 Carriage
70 X-ray bundle
93 End of stroke
94 End of stroke

The invention claimed is:

1. A method of limiting an X-ray beam, comprising:
providing a blade limiting device having at least two blades; and
moving the at least two blades using only an actuator, so as to produce an X-ray beam having a desired shape, wherein the actuator moves the at least two blades at a same time, in a direct way and in a same direction, even in an event of inversion of a direction of movement of the at least two blades.

2. The method according to claim 1,
wherein the at least two blades comprise a first blade and a second blade,
wherein the actuator moves the first blade, which in turn moves the second blade owing to a friction device,
wherein a movement occurring in any of two opposed directions, right and left,
and wherein the movement of one of said at least two blades is stopped by at least one end of stroke arranged on a side and from another end of stroke arranged on an opposed side of said one of said at least two blades.

3. The method according to claim 1, further comprising obtaining both a horizontal collimation through a first one of two perpendicularly blade limiting devices and a vertical collimation through a second one of the two perpendicularly blade limiting devices by overlapping the first one and the second one of the two perpendicularly blade limiting devices.

4. The method according to claim 3, further comprising providing a punched plate for the vertical collimation, the punched plate having a plurality of windows with different shapes and dimensions, the punched plate being linked to the actuator by a friction device, and being limited in translation movements by at least an end of stroke cooperating with each of both sides oriented toward one of two opposed directions of translation.

5. The method according claim 4, wherein, once a respective disposition of the at least two blades and of the punched plate is fixed, the two perpendicularly blade limiting devices synchronously rotate with an X-ray source and a sensor, so as to irradiate a limited portion of a dental arch of a patient under investigation.

6. The method according to claim 1,
wherein the at least two blades comprise a first blade and a second blade, and
wherein the first blade and the second blade are displaced along a direction perpendicular to an axis of rotation of an X-ray unit comprising a source and a sensor provided on opposite directions of an object to be imaged,
further comprising providing stops cooperating with the second blade and at a predetermined distance one from the other, said stops defining a path of a predetermined length for the second blade, along which the second blade and the first blade, move together maintaining a relative distance of facing ends of the first blade and the second blade and translating an aperture for passing of an X-ray beam relative to an axis of propagation of the X-ray beam, while optionally a common displacement of the first blade and the second blade is carried out by synchronizing the common displacement with a roto-translational movement of an X-ray group comprising a source and a sensor positioned on opposite sides of an object to be scanned.

7. A device limiting an X-ray beam emitted from an X-ray source, comprising:
a first device including:
at least two blades configured to collimate an X-ray beam, so as to produce an X-ray beam having a desired shape, the at least two blades comprising a first blade and a second blade;
an actuator moving the at least two blades in a same direction with continuity, even under a condition of inversion of a movement direction;
a friction device; and
at least an end of stroke, wherein a movement of the first blade causes a movement of the second blade by interposing the friction device between the first blade and the second blade, and
wherein the movement of the second blade is limited on both sides oriented to one of two opposed translation direction, respectively, by the at least an end of stroke cooperating with one of said both sides, respectively.

8. The device according to claim 7,
further comprising:
a second device including:
at least two blades configured to collimate an X-ray beam, so as to produce an X-ray beam having a desired shape, the at least two blades comprising a first blade and a second blade;
an actuator moving the at least two blades in a same direction with continuity, even under a condition of inversion of a movement direction;
a friction device;
at least an end of stroke;
wherein a movement of the first blade causes a movement of the second blade by interposing the friction device between the first blade and the second blade, and
wherein the movement of the second blade is limited on both sides oriented to one of two opposed translation directions, respectively, by the at least an end of stroke cooperating with one of said both sides, respectively,
wherein the first device is configured to control a horizontal collimation, and
wherein the second device is configured to control a vertical collimation, the first device and the second device being perpendicularly set and overlapping each other.

9. The device according to claim 7, further comprising a punched plate comprising a plurality of windows of different shapes and dimensions, wherein a horizontal collimation is obtained through a movement of the at least two blades, and wherein a vertical collimation is obtained with the punched plate, the plurality of windows superimposing over a window defined by the at least two blades.

10. The device according to claim 9, wherein the at least two blades and the punched plate are rolled to form concentric cylinders, and wherein the punched plate forms an outer cylinder, and the at least two blades slide on internal cylinders.

11. The device according to claim 9, further comprising an X-ray source and a sensor.

12. The device according to claim 11, further comprising:
an X-ray unit,
wherein a roto-translational movement of the X-ray unit is synchronized with a displacement of the first blade and the second blade along a portion of a path between stops for the second blade.

13. A method of limiting an X-ray beam, wherein at least two blades of a blade limiting device are moved by only an actuator, so as to produce an X-ray beam having a desired shape, the at least two blades being movable one with respect to the other changing a mutual distance, thereby varying a width of an aperture through which an X-ray beam passes, the aperture being delimited on two opposite sides by respectively one of the at least two blades, the method comprising:
displacing along a path of a predefined length the at least two blades together with the actuator in a first direction and a second direction, the second direction being opposite to the first direction;
displacing a second blade of the at least two blades relative to a first blade of the at least two blades along a predefined path, thus enabling a distance between the at least two blades to be varied, either increased or decreased;
linking the first blade to the actuator with a rigid link, thereby maintaining the same relative position in relation to the actuator;
linking the second blade to the actuator with a friction device interposed between the second blade and the rigid link, the friction device allowing the second blade to be displaced relative to the rigid link to the actuator; and
providing a stop device that cooperates respectively with a leading edge of the second blade relatively to two opposed directions, thereby preventing a common displacement of the second blade in any of the two opposed directions with the first blade for a length of a path of the first blade.

14. A device limiting an X-ray beam emitted from an X-ray source, comprising:
at least two blades comprising a first blade and a second blade configured to collimate an X-ray beam;
an actuator moving the at least two blades in a same direction, even under a condition of inversion of a movement direction;
a friction device;
a rigid link; and
at least an end of stroke,
wherein the first blade is rigidly linked to the actuator such that the first blade maintains a relative position in relation to the actuator, and
wherein the second blade is linked to the single by interposing the friction device between the second blade and the rigid link to the actuator, and a movement of the second blade in common with the first blade is limited on both sides of the second blade, which are oriented toward one of two opposed translation directions, respectively, by the at least an end of stroke cooperating with one of said both sides.

15. The device according to claim 14, further comprising:
an X-ray unit comprising a source and a sensor positioned on opposite sides of a target; and
stops positioned within two opposite ends of a first path of the first blade, the stops having a distance defining a second path of displacement for the second blade, the second path being shorter than the first path and corresponding to a portion of an entire path of displacement of the first blade, wherein, during a displacement along a portion of first path, the first blade and the second blade are displaced together without changing their relative position in a direction of displacement, and wherein the direction of displacement is perpendicular to a common axis of roto-translation of the X-ray unit.

* * * * *